(12) United States Patent
Wang et al.

(10) Patent No.: US 8,128,568 B2
(45) Date of Patent: Mar. 6, 2012

(54) HANDHELD VOLUMETRIC ULTRASOUND SCANNING DEVICE

(75) Inventors: Shih-Ping Wang, Los Altos, CA (US);
Douglas G. Summers, Palo Alto, CA (US); Jiayu Chen, Palo Alto, CA (US);
Tor C. Anderson, Los Gatos, CA (US)

(73) Assignee: U-Systems, Inc., Sunnyvale, CA (US)

( * ) Notice: Subject to any disclaimer, the term of this patent is extended or adjusted under 35 U.S.C. 154(b) by 832 days.

(21) Appl. No.: 12/238,091

(22) Filed: Sep. 25, 2008

(65) Prior Publication Data

US 2009/0024039 A1 Jan. 22, 2009

Related U.S. Application Data

(63) Continuation-in-part of application No. 11/757,996, filed on Jun. 7, 2007, application No. 12/238,091, which is a continuation-in-part of application No. PCT/US2007/010753, filed on May 2, 2007.

(60) Provisional application No. 60/746,259, filed on May 2, 2006, provisional application No. 61/081,204, filed on Jul. 16, 2008, provisional application No. 60/803,762, filed on Jun. 2, 2006.

(51) Int. Cl.
*A61B 8/00* (2006.01)
(52) U.S. Cl. .................... 600/459; 600/446; 345/1.1
(58) Field of Classification Search .......... 600/446, 600/459; 345/1.1
See application file for complete search history.

(56) References Cited

U.S. PATENT DOCUMENTS 5,199,437 A * 4/1993 Langberg ............... 600/463
(Continued)

OTHER PUBLICATIONS

Howard et al., "An Electronic Device for Needle Placement During Sonographically Guided Percutaneous Intervention," Radiology 218: 905-911 (2001).

(Continued)

*Primary Examiner* — Brian Casler
*Assistant Examiner* — Jonathan Cwern
(74) *Attorney, Agent, or Firm* — Cooper & Dunham, LLP

(57) ABSTRACT

An apparatus and related methods for ultrasonically scanning a tissue volume are described, the apparatus being particularly advantageous in the context of freehand ultrasound assisted biopsy of the breast although readily applied to non-biopsy contexts and other body parts. The apparatus comprises a casing configured and dimensioned for single-handed manipulation relative to a surface of the tissue, and a texturably couplant-porous material sheet extending across an opening of the casing. The texturably couplant-porous material sheet has an outer side and an inner side relative to the casing, the outer side for compressively contacting the tissue surface. The apparatus further comprises an ultrasound transducer positioned against the inner side of the texturably couplant-porous material sheet and being mechanically translatable thereacross for volumetrically scanning the tissue volume therethrough.

6 Claims, 6 Drawing Sheets

U.S. PATENT DOCUMENTS

| | | | |
|---|---|---|---|
| 5,494,038 A * | 2/1996 | Wang et al. | 600/459 |
| 5,526,812 A | 6/1996 | Dumoulin et al. | |
| 5,997,481 A * | 12/1999 | Adams et al. | 600/459 |
| 6,027,457 A | 2/2000 | Shmulewitz et al. | |
| 6,216,029 B1 | 4/2001 | Paltieli | |
| 6,689,067 B2 | 2/2004 | Sauer et al. | |
| 6,695,786 B2 | 2/2004 | Wang et al. | |
| 6,733,458 B1 | 5/2004 | Steins et al. | |
| 6,764,449 B2 | 7/2004 | Lee et al. | |
| 7,334,478 B2 | 2/2008 | Hwang | |
| 7,371,218 B2 | 5/2008 | Walston et al. | |
| 2003/0199765 A1 | 10/2003 | Stetten et al. | |
| 2003/0212327 A1 * | 11/2003 | Wang et al. | 600/437 |
| 2004/0267121 A1 | 12/2004 | Sarvazyan et al. | |
| 2006/0184034 A1 * | 8/2006 | Haim et al. | 600/459 |
| 2007/0016060 A1 | 1/2007 | Hwang | |
| 2008/0004526 A1 | 1/2008 | Gross | |

OTHER PUBLICATIONS

Stetton et al., "Tomographic Reflection to Merge Ultrasound Image with Direct Vision," IEEE Proceedings of the 2000 Applied Imagery Pattern Recognition (AIPR) Annual Workshop, pp. 200-205, (2000).

* cited by examiner

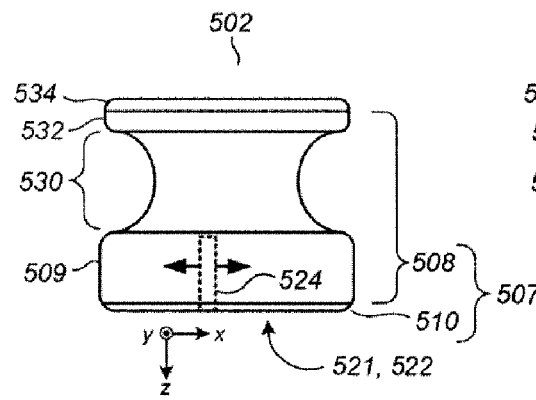
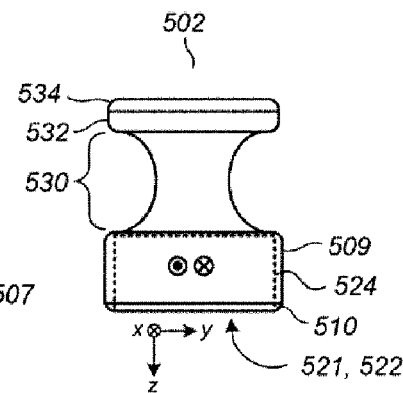
FIG. 5A  FIG. 5B
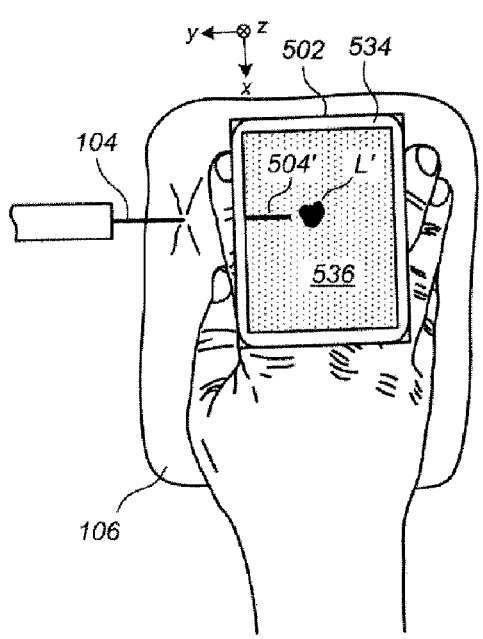
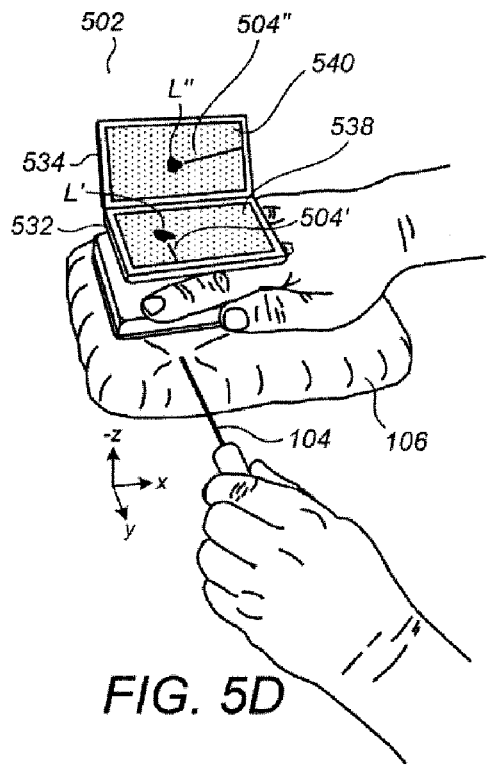
FIG. 5C  FIG. 5D

HANDHELD VOLUMETRIC ULTRASOUND SCANNING DEVICE

CROSS-REFERENCE TO RELATED APPLICATIONS

This patent application claims the benefit of U.S. Provisional Ser. No. 61/081,204, filed Jul. 16, 2008. This patent application is a continuation-in-part of U.S. Ser. No. 11/757,996, filed Jun. 4, 2007, which claims the benefit of U.S. Ser. No. 60/803,762, filed Jun. 2, 2006 and which published as US2007/028221A1 on Dec. 6, 2007. This patent application is also a continuation-in-part of PCT/US2007/010753, filed May 2, 2007, which claims the benefit of U.S. Ser. No. 60/746,259, filed May 2, 2006 and which published as WO2007/130526A2 on Nov. 15, 2007. Each of the above-referenced applications is incorporated by reference herein.

FIELD

This patent specification relates to the ultrasonic imaging of biological tissues. More particularly, this patent specification relates to a handheld volumetric ultrasound scanning device that, although advantageously usable in other applications as well, is particularly advantageous for use in image-guided freehand biopsy procedures.

BACKGROUND AND SUMMARY

Biopsy refers generally to the removal of a tissue sample from a living body for examination. In the field of breast cancer detection and treatment, breast tissue biopsies are often required when a suspicious lesion has been detected. Alternatives to traditional open surgical biopsy have been developed that are less invasive and, therefore, less risky and less costly. Percutaneous breast biopsy refers to the use of a biopsy needle or other instrument, usually long and relatively narrow, to puncture through the skin and capture cellular tissue associated with a breast lesion. The captured tissue is removed from the body and examined for a determination of whether the breast lesion represents a benign or malignant condition.

Percutaneous breast biopsy procedures include fine needle aspiration, core needle biopsy, and vacuum-assisted biopsy. In fine needle aspiration, a fine gauge needle (22 or 25 gauge) and a syringe are used to sample fluid from a breast cyst or remove clusters of cells from a solid mass. In core needle biopsy, small samples of tissue are removed using a hollow "core" needle. In vacuum-assisted biopsy, a special biopsy probe is inserted through a small opening in the skin. Unlike core needle biopsy, which requires several separate needle insertions to acquire multiple samples, the special biopsy probe used during vacuum-assisted biopsy is inserted only once for obtaining multiple samples. Vacuum-assisted biopsy is often referenced by the brand name of the biopsy instrument used, such as MAMMOTOME® from Johnson & Johnson Ethicon Endo-Surgery, MIBB® (Minimally Invasive Breast Biopsy) from Tyco International, Intact™ Breast Lesion Excision System from Intact Medical Systems, and Celero™ from Suros, a Hologic Company.

As used herein, the terms radiologist, physician, surgeon, clinician, and so forth are used interchangeably and generically to refer to medical professionals that analyze medical images and make clinical determinations therefrom, and/or that perform medical procedures under the at least partial guidance of medical imaging systems, it being understood that such person might be titled differently, or might have differing qualifications, depending on the country or locality of their particular medical environment. Percutaneous breast biopsy procedures are often performed with the assistance of ultrasound imaging to facilitate guidance of the biopsy instrument toward and into the breast lesion under study. In so-called freehand ultrasound assisted biopsy, the clinician holds an ultrasound transducer, typically a linear array transducer, against the skin with one hand while manipulating the biopsy instrument with the other hand, the clinician watching the biopsy instrument in real-time on the ultrasound monitor to help guide it to the lesion. In such applications, it is necessary to keep the biopsy needle positioned within the imaged plane in order for it to remain visible on the ultrasound monitor during the procedure.

For the highly skilled clinician, freehand ultrasound assisted biopsy of the breast using a linear array ultrasound transducer can be quickly performed in an out-patient environment, and is much less expensive than other breast biopsy procedures such as x-ray guided stereotactic biopsy and surgical biopsy. Although freehand ultrasound guided biopsy has become a highly popular procedure, it could become even more popular if it were easier to perform. Difficulties begin with the breast surface itself, which can be shifty beneath the linear array ultrasound transducer and even more so because of the slipperiness of the ultrasound gel. The clinician needs to manipulate the linear array ultrasound transducer in one hand and the biopsy needle in the other hand such that the biopsy needle, which can be relatively thin (approximately 1 mm in diameter), is maintained along with the breast lesion within the scan plane of the linear array ultrasound transducer to allow the biopsy needle and lesion to be visible on the ultrasound display. Moreover, the ultrasound display itself is often about three feet away from the breast and difficult to view simultaneously therewith.

It would be desirable to facilitate a freehand ultrasound assisted breast biopsy in a manner that improves one or more of image quality, thoroughness, patient comfort, sample quality, quickness of the process, and accessibility of the process to a wider range of clinicians of different skill levels. It is to be appreciated, however, that while one or more of the preferred embodiments described herein is particularly advantageous for facilitating freehand ultrasound assisted breast biopsy, there is ready applicability to a wide variety of medical imaging applications in which real-time three-dimensional ultrasound scanning is desirable such as, but not limited to, cardiac imaging and fetal imaging, both inside and outside the context of biopsy instrument guidance. Other issues arise as would be readily apparent to one skilled in the art in view of the present disclosure.

According to one preferred embodiment, provided is an apparatus for ultrasonically scanning a tissue volume having a tissue surface. The apparatus comprises a casing configured and dimensioned for single-handed manipulation relative to the tissue surface, and a texturably couplant-porous material sheet extending across an opening of the casing. The texturably couplant-porous material sheet has an outer side and an inner side relative to the casing, the outer side for compressively contacting the tissue surface. The apparatus further comprises an ultrasound transducer positioned against the inner side of the texturably couplant-porous material sheet and being mechanically translatable thereacross for volumetrically scanning the tissue volume therethrough. The incorporation of a texturably couplant-porous material sheet, which can comprise for example a taut fabric sheet or a vented membrane, advantageously tends to at least partially stabilize the tissue surface as the ultrasound transducer is swept thereacross, while also providing for high quality in the images derived from the volumetric ultrasound scans.

According to another preferred embodiment, provided is a method for performing percutaneous biopsy of a target lesion in a tissue volume, comprising manually maintaining a handheld ultrasound probe in compressive contact with a surface of the tissue volume, the handheld ultrasound probe comprising a texturably couplant-porous material sheet having a first side compressively contacting the surface and a second side opposite the first side, the handheld ultrasound probe further comprising an ultrasound transducer repetitively translated across the second side of the texturably couplant-porous material sheet to acquire volumetric ultrasound scans of the tissue volume therethrough. The method further comprises viewing ultrasound images of the target lesion and at least a portion of a freehand percutaneous biopsy instrument on an ultrasound display that is updated in real time with the acquisition of the volumetric ultrasound scans, and guiding the freehand percutaneous biopsy instrument toward the lesion based at least in part on the viewed ultrasound images.

According to another preferred embodiment, provided is an apparatus for ultrasonically scanning a tissue volume, comprising a processor and a handheld ultrasound device. The handheld ultrasound device comprises a casing configured and dimensioned for single-handed manipulation and a mechanically oscillated ultrasound transducer disposed therewithin. The casing has a top surface and a bottom opening. The handheld ultrasound device further comprises a membranous material sheet extending across the bottom opening for compressively contacting a surface of the tissue volume, the ultrasound transducer being mechanically translated across the material sheet while in contact therewith, the ultrasound transducer acquiring ultrasonic scans of the tissue volume downward through the material sheet during the mechanical translation. The processor processes the ultrasonic scans to generate an ultrasound volume representative of an ultrasonic property of the tissue volume. The handheld ultrasound device further comprises a first ultrasound display integral with an upper surface of the casing for displaying a first two-dimensional image derived from the ultrasound volume, and a lid hingably coupled to the casing near the first ultrasound display, the lid being manually closable to cover the first display and manually openable to uncover the first display and remain at a user-adjustable opening angle relative thereto. The handheld ultrasound device further comprises a second ultrasound display integral with an inner surface of the lid for displaying a second two-dimensional image derived from the ultrasound volume when the lid is in an open position. The handheld ultrasound device further comprises an angle detection device for detecting the opening angle of the lid. Preferably, the processor computes the first two-dimensional image by compositing the ultrasound volume in a generally upward direction, and computes the second two-dimensional image by receiving the detected opening angle and compositing the ultrasound volume in a first direction faced by the second ultrasound display as determined by the detected opening angle.

BRIEF DESCRIPTION OF THE DRAWINGS

FIGS. 5A and 5B illustrate side and front views, respectively, of a handheld ultrasound scanning apparatus according to a preferred embodiment;

FIG. 5C illustrates a top view of the handheld ultrasound scanning apparatus of FIGS. 5A-5B facilitating freehand ultrasound assisted biopsy according to a preferred embodiment;

FIG. 5D illustrates a perspective view of the handheld ultrasound scanning apparatus of FIGS. 5A-5B facilitating freehand ultrasound assisted biopsy according to a preferred embodiment;

DETAILED DESCRIPTION

Figure 1A:
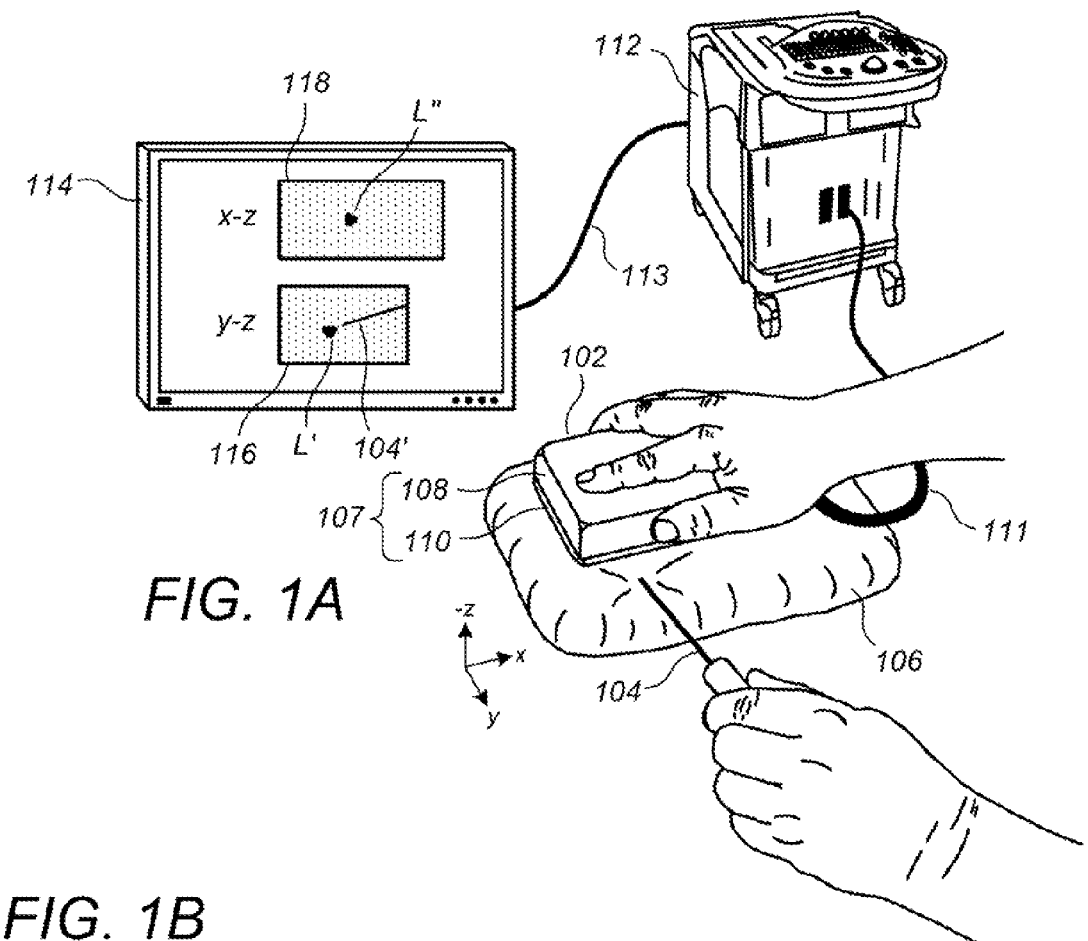
FIG. 1A illustrates a perspective view of a handheld ultrasound scanning apparatus according to a preferred embodiment facilitating freehand ultrasound assisted biopsy according to a preferred embodiment.
Figure 1B:
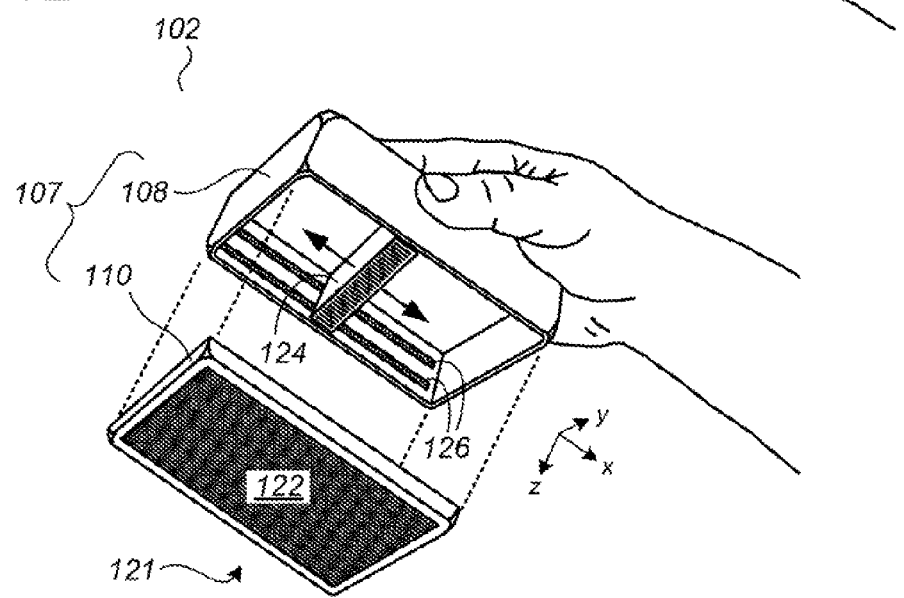
FIG. 1B illustrates an exploded perspective view of the handheld ultrasound scanning apparatus of FIG. 1A.

FIG. 1A illustrates a perspective view of a handheld ultrasound scanning apparatus 102 according to a preferred embodiment facilitating freehand ultrasound assisted biopsy according to a preferred embodiment, a tissue phantom 106 representing the breast of a supine patient. FIG. 1B illustrates an exploded perspective view of the handheld ultrasound scanning apparatus 102. It is to be appreciated that although freehand ultrasound-assisted breast biopsy represents a particularly advantageous use of the handheld ultrasound scanning apparatus 102, and although the handheld ultrasound scanning apparatus 102 is further described hereinbelow in the particular context of freehand ultrasound-assisted breast biopsy, there are many other volumetric ultrasound imaging applications that are within the scope of the preferred embodiments, including freehand ultrasound-assisted biopsy of other body parts, and including volumetric ultrasound imaging in non-biopsy contexts for the breast and/or other body parts. Also illustrated in FIG. 1A is a biopsy instrument 104 that may be used in conjunction with the handheld ultrasound scanning apparatus 102 according to a preferred embodiment. Although shown as a needle-type biopsy instrument in the example of FIG. 1A, it is to be appreciated that the biopsy instrument 104 can generally be any of a variety of different surgical instruments for which ultrasound-assisted visualization is desired including, but not limited to, fine needle aspiration instruments, core needle biopsy instruments, and vacuum-assisted biopsy instruments.

Handheld ultrasound scanning apparatus 102 comprises a casing 107 that is configured and dimensioned for single-handed manipulation. For the example of FIG. 1A, the handheld ultrasound scanning apparatus 102 is coupled by a connector cable 111 to an ultrasound processing unit 112, which is coupled by a video cable 113 to a display unit 114. The display unit 114 can optionally include touchscreen capability for receiving user inputs. In other preferred embodiments, wireless communication link (e.g., bluetooth, infrared, etc.) are used to link the handheld ultrasound scanning apparatus 102 with the ultrasound processing unit 112 and/or to link the ultrasound processing unit 112 to the display unit 114. In still other preferred embodiments as described further infra, one or both of the ultrasound processing unit 112 and display unit 114 are in miniaturized form and integral with the handheld ultrasound scanning apparatus 102. An opening 121 is formed in casing 107 across which is disposed a texturably couplant-porous material sheet 122. The texturably couplant-porous material sheet 122 has an inner side that faces inward with respect to the casing and an outer side that faces outward with respect to the casing. The handheld ultrasound scanning apparatus 102 further comprises an ultrasound transducer 124 disposed within the casing 107 that contacts the inner side of the texturably couplant-porous material sheet 122 and that mechanically translates thereacross to scan the tissue volume therethrough.

For one preferred embodiment, the texturably couplant-porous material sheet 122 comprises a taut fabric sheet having with material properties similar to those described in the commonly assigned WO2007/014292A2, which is incorporated by reference herein. As used herein, fabric refers generally to a material structure of interconnected parts, such as can be formed by knitting, weaving, or felting natural or synthetic fibers, assembling natural or synthetic fibers together into an interlocking arrangement, fusing thermoplastic fibers, or bonding natural or synthetic fibers together with a cementing medium, and further refers to materials having similar textures or qualities as those formed thereby, such as animal membranes or other naturally occurring substances having fabric-like properties (either inherently or by processing), and such as materials generated by chemical processes yielding fabric-like webbings. In one preferred embodiment, the taut fabric sheet is substantially inelastic. Preferably, the taut fabric sheet is sheer to allow visibility therethrough, as may be advantageous where (a) the casing 107 is optically transparent to allow visibility of the skin surface thereunderneath, or (b) even if the casing 107 is not optically transparent, allowing viewing of the inner workings of the handheld device through the taut fabric sheet. One particularly suitable material for the taut fabric sheet comprises a polyester organza material having a filament diameter of about 40-microns and a filament spacing of about 500 microns. However, the taut fabric sheet may comprise any of a variety of other fabrics that are substantially inelastic and generally porous to ultrasound couplants without departing from the scope of the present teachings. Examples include, but are not limited to, polyester chiffon fabrics and cloth fabrics comprising straight weaves of substantially inelastic fibers. Where the weave is particularly tight (for example, the cloth used in men's dress shirts or the cloth used in many bed sheets), porosity can be achieved by perforating the cloth or otherwise introducing irregularities that allow the ultrasound couplant to soak or seep through.

As an alternative to a taut fabric sheet, or in combination therewith, the texturably couplant-porous material sheet 122 can comprise a vented membrane as described in WO2007/014292A2, supra, in which a membraneous material is patterned with voids therethrough to provide porosity to acoustic couplant. Examples of materials that can be used for the vented membrane include, but are not limited to, polypropylene, polyester (including but not limited to Mylar), polyethylene, PTFE, PET, paper, Kevlar, metal, and epoxy-fiber composite materials. Preferably, the size of the voids and the average void pitch is equal to or greater than the wavelength of the acoustic signals being applied. By way of example, for a 7 MHz ultrasound frequency, the size of the voids should be about 0.5 mm or greater. The vented membrane can be formed, for example, by beginning with a uniform film sheet and establishing a void pattern therein by one of stamping, perforating, or other process designed to establish a void pattern. Examples include laser perforation, perforation using hot needles, die cutting, cold stamping, and hot-stamping. For one preferred embodiment, the vented membrane comprises a film sheet less than 1 mm thick, with at least 25% of a surface area of the film sheet being occupied by voids. In another preferred embodiment, at least 80% of the surface area is occupied by voids. In an alternative fabrication method, the vented membrane can be formed by a vertical fusing of a first monofilamental pattern and a second monofilamental pattern. In one example, each monofilamental pattern can comprise 0.04 mm monofilaments having a pitch of about 0.5 mm.

In comparison to the use of a material that is not couplant-porous at the interface between the ultrasound transducer 124 and the skin surface, the texturably couplant-porous material sheet 122 provides for higher image quality for at least the reason that it promotes dissipation of air bubbles that might otherwise form at that surface. Notably, whereas the taut fabric sheet(s) and vented membrane(s) in WO2007/014292A2, supra, are incorporated into relatively wide-area compressive surfaces for static wide-area dual-handed and/or mechanically supported breast stabilization, it has been found that such texturably couplant-porous materials can also be advantageously applied in the context of handheld volumetric scanning in which there is a unique blend of desirable performance criteria. More particularly, when wetted with acoustic couplant, it has been found that the texturably couplant-porous material sheet 122 takes on a uniquely desirable combination of slidability over the skin, on the one hand, when there is a slightly lesser downward (skinward) compressive force as the clinician moves the device around or toward the area of interest, and grippability of the skin, on the other hand, when there is a slightly greater downward (skinward) compressive force as the clinician holds the device still over a location of particular interest, as when a particular three-dimensional subvolume is to be stabilized for high-quality volumetric imaging and/or for the manipulation of the biopsy needle relative to a lesion in that subvolume.

Preferably, the texturably couplant-porous material sheet 122 is wetted with an acoustic couplant facilitating acoustic coupling between the ultrasound transducer 124 and the tissue sample. This can be achieved by pre-impregnating the texturably couplant-porous material sheet 122 prior to contact with the skin surface, applying the acoustic couplant to the skin surface prior to contact by handheld ultrasound scanning apparatus 102, or both.

According to a preferred embodiment, the casing 107 comprises a housing 108 that houses the ultrasound transducer 124, and a frame 110 across which the texturably couplant-porous material sheet 122 is extended. The frame 110 is configured and dimensioned to be mateably connectable to the housing 108, the frame 110 establishing the opening 121 of the casing 107 when connected to the housing 108. For one preferred embodiment, the texturably couplant-porous material sheet 122 is affixed to the frame 110, and the frame 110 is removably mateable to the housing (for example, click-on and click-off) by the clinician or an assistant, whereby the frame 110 and texturably couplant-porous material sheet 122 form a single disposable element than can be removed and replaced between patients.

Illustrated in FIG. 1B are guide rails 126 that form part of an overall electromechanical actuation assembly (not shown) for repetitively translating the ultrasound transducer 124 within the housing 108 in a back and forth manner across and in contact with the inner side of the texturably couplant-porous material sheet 122, as indicated by the arrows pointing in the positive-x and negative-x direction in FIG. 1B. The electromechanical actuation assembly will generally include small electrical motors (minimotors, micromotors) mounted on the ultrasound transducer 124 and/or the housing 108 along with gears, belts, linear encoders, etc. as necessary to actuate the ultrasound transducer 124 in the manner(s) described herein, usually under the control of a control processor (not shown). Examples of actuation assembly technology that may be suitable for use in the handheld ultrasound scanning apparatus 102 are described in US07334478B2 and US20070016060A1, each of which is incorporated by reference herein. The actuation assembly technology may alternatively be similar to that used in certain commercially available real-time 3D ("live 3D," "4D") ultrasound scanning probes such as the Voluson 730 probe available from General Electric Medical Systems.

According to one preferred embodiment, the display unit 114 displays, under the control of a display processor within the ultrasound processing unit 112, a first image 116 corresponding to a first plane generally parallel to the scan plane of the ultrasound transducer 124 and passing through the target lesion L, for providing an image L' of the target lesion along with an image 104' of the biopsy instrument when it is maintained in that plane by the clinician. The display unit 114 further displays a second image 118 generally perpendicular to both the first plane and the texturably couplant-porous material sheet and passing through the target lesion L for providing an image L" of the target lesion, along with an image (not shown) of the biopsy instrument 104, which would appear as a point object if and when it pierces that plane. Optionally, automated needle segmentation and beam-steering techniques can be used to cause the biopsy instrument 104 to appear more brightly in the displayed images, as described in the commonly assigned US06524247B2, which is incorporated by reference herein. Any of a variety of volumetric image processing and display techniques, including automated lesion segmentation and recognition, automated biopsy instrument segmentation and recognition, automated biopsy instrument tracking, two-dimensional and three-dimensional projection algorithms, image superposition methods, predictive biopsy instrument display, and so forth can be used for optimal visual communication of the biopsy instrument 104 relative to the target lesion L. Examples of such techniques are described in US2007/028221A1 and WO2007/130526A2, supra. Other examples are discussed in US06216029B1, US06733458B1, US06764449B2, and, each of which is incorporated by reference herein.

In one preferred embodiment, the size of the opening 121 and the texturably couplant-porous material sheet 122 is approximately 6 cm in a direction parallel to the linear transducer array of the ultrasound transducer 124 (i.e., in the y-direction of FIGS. 1A-1B) and 9 cm along the direction of translation of the ultrasound transducer 124 (i.e., in the x-direction of FIGS. 1A-1B), and the ultrasound transducer 124 is repetitively translated at a rate in the range of 0.5 Hz (sweeps per second) to 30 Hz. The ultrasound display 114 is preferably refreshed as each sweep of the ultrasound transducer 124 acquires the most current data volume. A wide variety of sizes and shapes for the opening 121 and texturably couplant-porous material sheet 122 consistent with the handheld character of the handheld ultrasound scanning apparatus 102 are within the scope of the preferred embodiments, including 4 cm×4 cm, 4 cm×3 cm, 4 cm×2 cm, 3 cm×3 cm, 3 cm×2 cm, and other sizes. Particularly for smaller-area preferred embodiments and/or preferred embodiments in which the translation distance is kept relative small (e.g., a few centimeters or less), the volumetric scanning rate (and corresponding display refresh rate) can optionally be made even higher than 30 Hz.

Figure 2A:
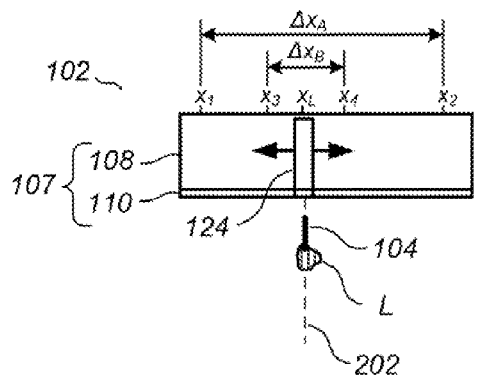
FIGS. 2A and 2B illustrate side and front views, respectively, of the handheld ultrasound scanning apparatus of FIGS. 1A and 1B facilitating freehand ultrasound assisted biopsy according to a preferred embodiment.
Figure 2B:
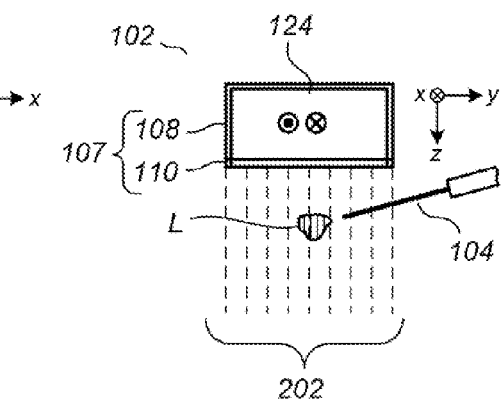

FIGS. 2A and 2B illustrate side and front cut-away views, respectively, of the handheld ultrasound scanning device 102 during operation, including a conceptual view of the lesion L and a scan plane 202 passing through the lesion L. According to one preferred embodiment, a preliminary "survey," "scout," or "exploratory" sweep mode is provided in which the ultrasound transducer is oscillatorily swept by a larger distance AXA (for example, 3 cm-9 cm) between a first set of endpoints $x_1$ and $x_2$ at a relatively slow rate (e.g., between 0.5 Hz-3 Hz) to image a larger volume of the tissue. This larger volume is then processed perceptually by the clinician based on the user display and/or automatically by the processing unit 112 to segment the location and shape of the lesion L. Based on this processing, a second set of endpoints $x_3$ and $x_4$ separated by a lesser distance $\Delta x_B$ (for example, 0.5 cm-1 cm) are determined that encompass the target lesion L. This determination can be made by receiving user inputs identifying those endpoints and/or from the automated segmentation process. The ultrasound transducer is then oscillatorily swept across the lesser distance $\Delta x_B$ between the second endpoints $x_3$ and $x_4$ at a relatively fast rate (e.g., 10 Hz or higher) to allow higher frame rates for a smaller volume of the tissue, which can be particularly useful as the tip of the biopsy instrument 104 closes in upon the lesion L and as the biopsy samples are taken. Preferably, the clinician or their assistant may enter override parameters at any chosen time to manually dictate the endpoints of the oscillatory sweeps and the scanning rate. Notably, the scanning rate can optionally be set to zero, in which case the handheld ultrasound scanning apparatus 102 may be operated in a manner similar to a conventional linear array transducer, albeit with the added advantages of having the texturably couplant-porous material sheet 122 positioned between the transducer surface and the skin surface.

Figure 3:
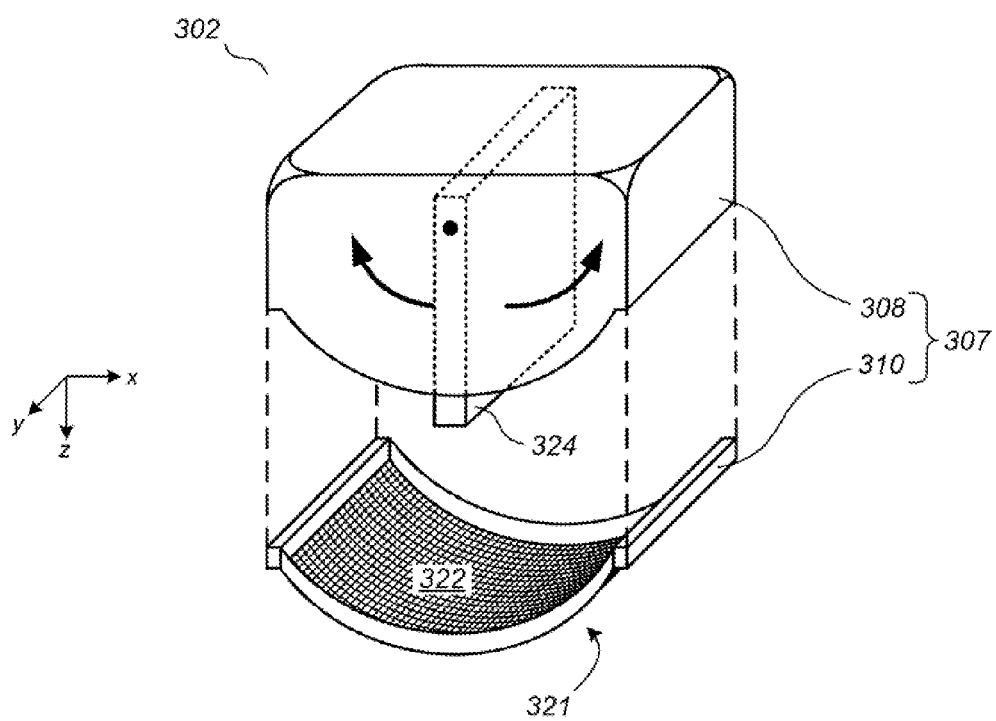
FIG. 3 illustrates a perspective view of a handheld ultrasound scanning apparatus according to a preferred embodiment.

FIG. 3 illustrates a perspective view of a handheld ultrasound scanning apparatus 302 according to a preferred embodiment, comprising an ultrasound transducer 324, and further comprising a casing 307 configured and dimensioned for single-handed manipulation, the casing 307 including a housing 308 and a removably mateable frame 310 defining an opening 321 across which is extended a texturably couplant-porous material sheet 322. The housing 308 and frame 310 are configured such that the texturably couplant-porous material sheet 322 extends convexly outward with respect an inside of the casing 307. A scanning face of the ultrasound transducer 324 is mechanically translatable, by swingable actuation of the ultrasound transducer 324, in the x-direction along the outwardly convex surface of the texturably couplant-porous material sheet 322. As an alternative to swingable actuation, the ultrasound transducer 324 can alternatively be translated along curved guide rails.

Figure 4:
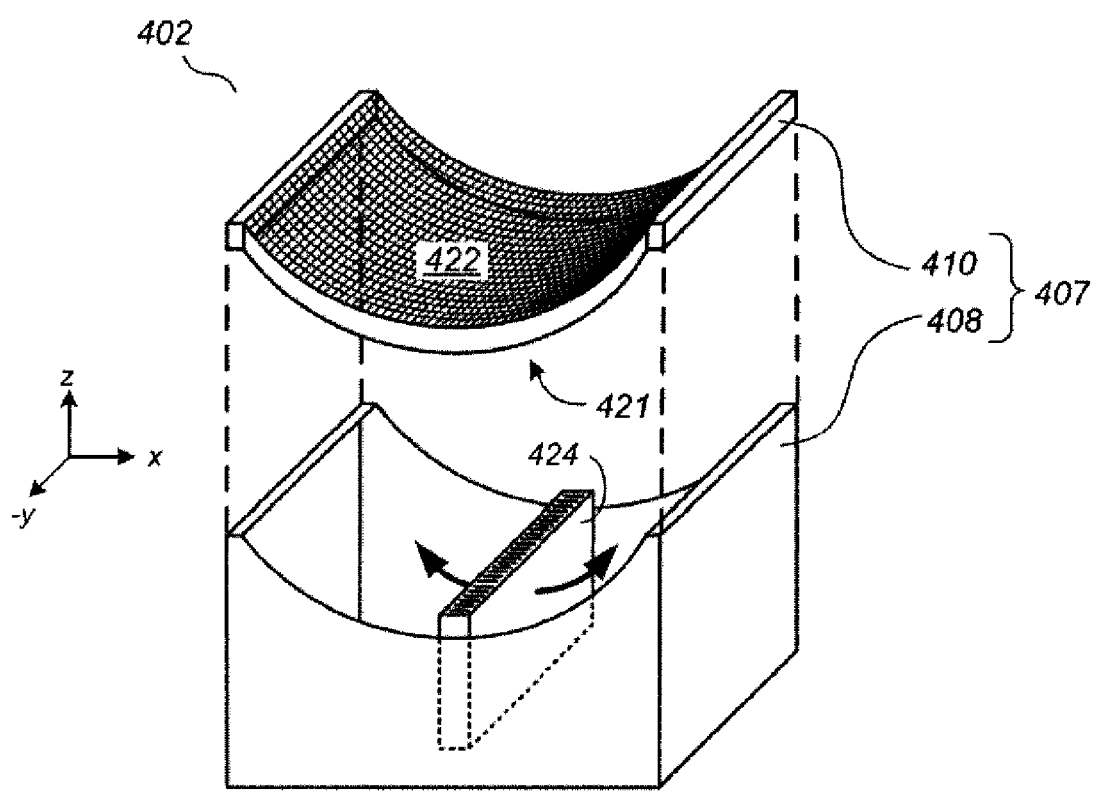
FIG. 4 illustrates a perspective view of a handheld ultrasound scanning apparatus according to a preferred embodiment.

FIG. 4 illustrates a perspective view of a handheld ultrasound scanning apparatus 402 according to a preferred embodiment, comprising an ultrasound transducer 424, and further comprising a casing 407 configured and dimensioned for single-handed manipulation, the casing 407 including a housing 408 and a removably mateable frame 410 defining an opening 421 across which is extended a texturably couplant-porous material sheet 422. The housing 408 and frame 410 are configured such that the texturably couplant-porous material sheet 422 extends convexly inward with respect an inside of the casing 407. The ultrasound transducer 424 is mechanically translatable along curved guide rails (not shown) in the x-direction along the inwardly concave surface of the texturably couplant-porous material sheet 422.

FIGS. 5A and 5B illustrate side and front views, respectively, of a handheld ultrasound scanning apparatus 502 according to a preferred embodiment. FIGS. 5C and 5D illustrate top and perspective views, respectively, of the handheld ultrasound scanning apparatus 502 facilitating freehand ultrasound assisted biopsy according to a preferred embodiment. Handheld ultrasound scanning apparatus 502 comprises an ultrasound transducer 524, and further comprises a casing 507 configured and dimensioned for single-handed manipulation, the casing 507 including a housing 508 and a removably mateable frame 510 defining an opening 521 across which is extended a texturably couplant-porous material sheet 522. The housing 508 has a lower end 509, an upper end 532, and a neck region 530 therebetween. The neck region 530 is narrowably contoured relative to the lower end 509 and upper end 532 and dimensioned such that the casing 507 is grippable at the neck region between two fingers of the hand of the clinician, as illustrated in FIGS. 5C and 5D. Depending on their personal preference, the clinician may alternatively elect to grip the casing 507 between their thumb and one of their fingers.

The handheld ultrasound scanning apparatus 502 of FIGS. 5A-5D can generally be used by either right-handed or left-handed clinicians without modifications between right-handed and left-handed use. The particular example of FIGS. 5C-5D generally corresponds to use by a left-handed clinician, with the handheld ultrasound scanning apparatus 502 being held by the right hand while the biopsy instrument 104 is manipulated by the left hand. Generally speaking, use by right-handed clinicians (not shown) will entail holding the handheld ultrasound scanning apparatus 502 with the left hand while manipulating the biopsy instrument 104 with the right hand.

Handheld ultrasound scanning apparatus 502 further comprises a clamshell-style lid 534 coupled to the upper end 532 of the casing 507, the lid 534 including a display screen 536 integral therewith and positioned thereon so as to be viewable by the clinician while performing the single-handed manipulation of the unit when the lid 534 is in a closed position. In operation according to one preferred embodiment as illustrated in FIG. 5C, the display screen 536 displays a two-dimensional image representative of a scene of the biopsy instrument 104 and lesion L that would be perceived by a hypothetical acoustic impedance camera positioned directly above the handheld ultrasound scanning apparatus 502 during the procedure (i.e., positioned some distance along the negative-z axis in the coordinate system of FIG. 5 and looking downward in the positive-z direction toward the scene), wherein such hypothetical acoustic impedance camera would be able to "see" acoustic impedance, rather than light, emanating from the tissue volume of interest. Such two-dimensional can be achieved, for example, by computing a maximum intensity projection (MIP) image in the z-direction from the acquired ultrasound volume, although other image composition methods including those based on automated lesion and/or needle segmentation can be used. Alternatively or in conjunction therewith, the display screen 536 can be used for displaying any particular subsurface x-y plane or slabbed adjacent group of subsurface x-y planes passing through or near the target lesion, or any of a variety of other useful biopsy-assisting views.

Referring now to FIG. 5D, handheld ultrasound scanning apparatus 502 further comprises a display screen 538 integral with the upper end 532 and a display screen 540 integral with an inner side of the lid 534 such that the display screens 538 and 540 are adjacently viewable by the clinician when the lid 534 is in an open position. In operation according to one preferred embodiment as illustrated in FIG. 5D, the display screen 538 displays a first two-dimensional image analogous to that of the display screen 536 of FIG. 5C, i.e., representative of a scene of the biopsy instrument 104 and lesion L that would be perceived from a hypothetical acoustic impedance camera that is positioned directly above the biopsy scene. Preferably, the display screen 540 displays a second two-dimensional image representative of a scene of the biopsy instrument 104 and lesion L that would be perceived from a hypothetical acoustic impedance camera positioned some distance in the negative-x direction relative to the lesion under biopsy and looking in the +x direction toward the scene, which can be composited in a manner similar to the first two-dimensional image except along the x-direction instead of the z-direction. The clinician can then use the first and second two-dimensional images, which include images L' and L" of the lesion, respectively, and images 504' and 504" of the biopsy instrument 104, respectively, for real-time guidance of the biopsy instrument 104 relative to the lesion. Alternatively or in conjunction therewith, the display screen 538 may display any particular subsurface x-y plane or slabbed adjacent group of subsurface x-y planes passing through or near the target lesion, while the display screen 540 may display any particular y-z plane or slabbed adjacent group of y-z planes passing through or near the target lesion. Among other advantages, the clinician is not required to look away from the area of their hands to view the assistive ultrasound images during the freehand ultrasound-assisted biopsy procedure.

The clamshell-style lid 534 is preferably openable and closeable in a manner similar to the lids of notebook computers, flip-phones, and so forth, and may optionally be rotatable once it has been opened, as with the lids of certain notebook computers, so that the display 540 can face a different way. For one preferred embodiment, one or more of the display screens 536, 538, and 540 can be similar to the touchscreens provided with iPhones, BlackBerries, and similar devices to allow for control inputs along with their display capabilities. For one preferred embodiment, the handheld ultrasound scanning apparatus 502 is entirely self-contained, with an onboard power source, ultrasound beamformers, processors, and controllers such that no communication with an external unit is required. For another preferred embodiment, the handheld ultrasound scanning apparatus 502 can be partially self-contained in that it comprises an onboard power source and is wirelessly connected to external processors/controllers. For still another preferred embodiment, the handheld ultrasound scanning apparatus 502 is connected by one or more electrical and/or electrooptical cables to one or more external units that provide power, control, beamforming, ultrasound processing, and display processing.

Figure 6A:
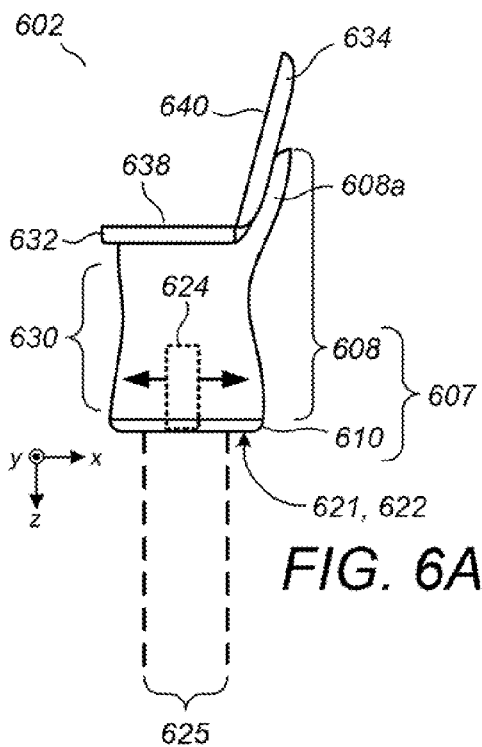
FIGS. 6A and 6B illustrate side and front views, respectively, of a handheld ultrasound scanning apparatus according to a preferred embodiment.
Figure 6B:
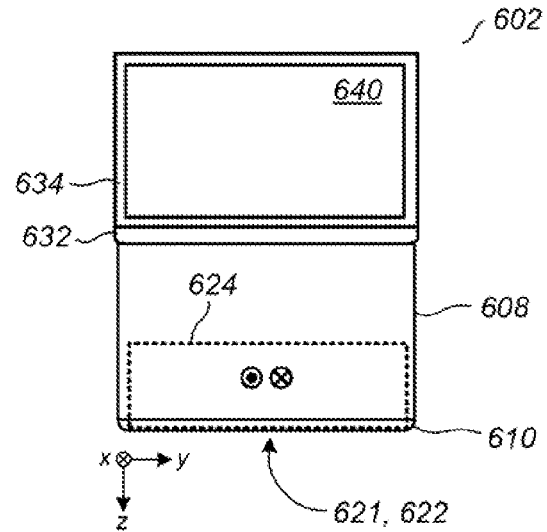
Figure 6C:
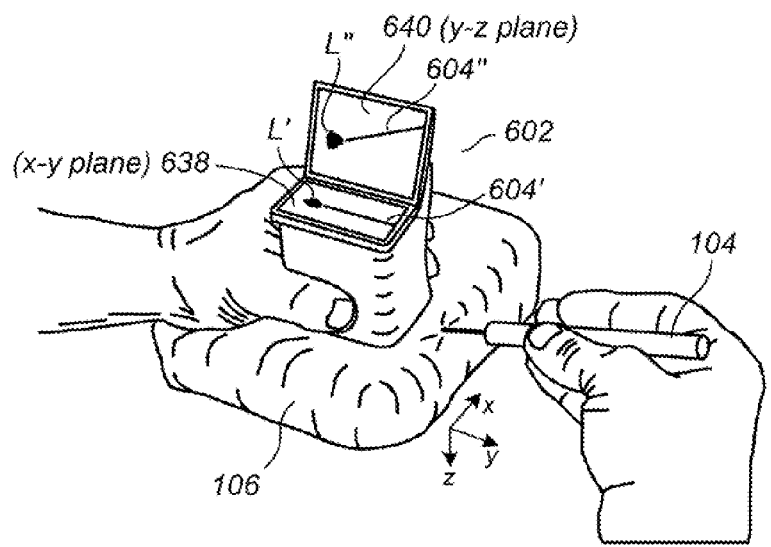
FIG. 6C illustrates a perspective view of the handheld ultrasound scanning apparatus of FIGS. 6A-6B facilitating freehand ultrasound assisted biopsy according to a preferred embodiment.

FIGS. 6A and 6B illustrate side and front views, respectively, of a handheld ultrasound scanning apparatus 602 according to a preferred embodiment. FIG. 6C illustrates top and perspective views, respectively, of the handheld ultrasound scanning apparatus 602 facilitating freehand ultrasound assisted biopsy according to a preferred embodiment. The handheld ultrasound scanning apparatus 602 is designed to have a look and feel reminiscent of a conventional handheld breast ultrasound linear array probe in terms of the way it is gripped and handled by the clinician, but provides a sufficient amount of automated translation of an ultrasound transducer 624 therewithin to enable useful three-dimensional imaging in a relatively narrow, slab-like region 625 thereunder. For one preferred embodiment, with respect to the exemplary coordinate system shown in FIGS. 6A-6C, the ultrasound transducer 624 is translated back and forth along the x-axis by about 2 cm or less, such that the slab-like region 625 correspondingly extends in the x-direction by about 2 cm or less. The slab-like region 625 extends in the y- and z-directions in a manner similar to that of a conventional linear array probe, i.e., according to the capabilities and settings of the ultrasound transducer 624. For another preferred embodiment, the translation distance of the ultrasound transducer 624 along the x-axis is limited to about 1 cm or less, with the slab-like region 625 correspondingly being limited to 1 cm or less. The handheld ultrasound scanning apparatus 602 is particularly advantageous for use for breast biopsy procedures in which it is known that the biopsy instrument 104 will be maintained in a relatively narrow slab-like region near the lesion being biopsied. By limiting the translation distance (i.e., the physical range in the x-direction that the ultrasound transducer 624 is translated), the translation frequency (i.e., the number of times the ultrasound transducer is translated back and forth per second) can be increased for obtaining higher volumetric frame rates (volume refreshes per second), which is particularly useful for procedures in which the biopsy instrument 104 might be moved around quickly. In one preferred embodiment, the translation frequency can be up to 30 translations per second for obtaining volumetric frame rates up to 30 translations per second when the translation distance is limited to about 1 cm.

In addition to the ultrasound transducer 624, the handheld ultrasound scanning apparatus 602 further comprises a casing 607, the casing 607 including a housing 608 and a removably mateable frame 610 defining an opening 621 across which is extended a texturably couplant-porous material sheet 622. The housing 608 extends from a lower end to an upper end 632 and includes a neck region 630 formed therebetween. The casing 607 is dimensioned with a relatively tall profile in the z-direction in comparison to the preferred embodiment of FIGS. 5A-5D, supra, and a narrow profile in the direction of translation of the ultrasound transducer 624 (i.e., narrow in the x-direction of FIGS. 6A-6C), such that the casing 607 is gripped and handled in a way that is more reminiscent of a conventional linear array probe.

Handheld ultrasound scanning apparatus 602 further comprises a first display screen 638 integral with the upper end 632 of the casing 607, and a clamshell-style lid 634 coupled to the upper end 632, the lid 634 coming to rest against a backstop feature 608a integral with the housing 608 when opened, the lid 634 including a second display screen 640 integral therewith. According to one preferred embodiment, the first display screen 638 extends in the y-direction by an amount commensurate with the width of the ultrasound probe 624 in the y-direction (for example, about 4 cm), while extending in the x-direction by an amount commensurate with the translation distance in the x-direction (for example, about 1 cm). For such preferred embodiment, the first display screen 638 thus has an aspect ratio of about 4:1. In other preferred embodiments, the aspect ratio of the first display screen 638 can be relaxed to only about 2:1 or greater.

In operation according to one preferred embodiment as illustrated in FIG. 6C, the first display screen 638 displays a first two-dimensional image representative of a scene of the biopsy instrument 104 and lesion L that would be perceived by a hypothetical acoustic impedance camera positioned directly above the handheld ultrasound scanning apparatus 602 during the procedure (i.e., positioned some distance along the negative-z axis in the coordinate system of FIG. 6 and looking downward in the positive-z direction toward the scene), wherein such hypothetical acoustic impedance camera would be able to "see" acoustic impedance, rather than light, emanating from the tissue volume of interest. As described supra with respect to FIGS. 5C-5D, this can be achieved by computing a maximum intensity projection (MIP) image in the z-direction from the acquired ultrasound volume, although other image composition methods including those based on automated lesion and/or needle segmentation can be used. Also according to a preferred embodiment, the second display screen 640 displays a second two-dimensional image representative of a scene of the biopsy instrument 104 and lesion L that would be perceived from such hypothetical acoustic impedance camera, wherein the hypothetical acoustic impedance camera is positioned some distance in the negative-x direction relative to the lesion under biopsy, the second two-dimensional image being composited in a manner similar to the first two-dimensional image except along the x-direction instead of the z-direction. The clinician can then use the first and second two-dimensional images, which include images L' and L" of the lesion, respectively, and images 604' and 604" of the biopsy instrument 104, respectively, for real-time guidance of the biopsy instrument 104 relative to the lesion. In other preferred embodiments, by way of example and not by way of limitation, the first display screen 638 may display any particular subsurface x-y plane or slabbed adjacent group of subsurface x-y planes passing through or near the target lesion, while the second display screen 640 may display any particular y-z plane or slabbed adjacent group of y-z planes passing through or near the target lesion.

As used herein, the term compositing refers broadly to any of a variety of techniques by which a three-dimensionally distributed property, such as acoustic impedance, is processed to produce a two-dimensional image that is a view of that three-dimensional distribution (or "scene") from a particular distal vantage point in space. The term composition angle, or direction of image compositing, refers to a vector direction between the distal vantage point and the three dimensional distribution ("scene"). Examples of methods for compositing include three-dimensional rendering techniques such as maximum intensity projection, minimum intensity projection, and ray casting, as well as other techniques such as slabbing along the direction of the composition angle, and further can include graphically overlaying a highlighted or iconic version of an object within the scene (such as a biopsy instrument) that was detected either intrinsically (such as by computer processing the volume to segment the biopsy instrument) or extrinsically (such as by gyroscopic or magnetic location of the biopsy needle) as that object would appear from the distal vantage point.

By contrasting the preferred embodiment of FIG. 6C, for which the display screen 640 faces approximately the same direction as the direction of compositing (the display screen 640 faces the negative-x direction and the MIP image displayed thereon was composited in the x-direction) with the preferred embodiment of FIG. 5D, for which the display screen 540 faces differently from the direction of compositing (the display screen 540 faces the negative-y direction while the MIP image displayed thereon was composited in the x-direction), it can be seen that the two-dimensional image on display screen 640 (FIG. 6) provides a more intuitive basis than that of display screen 540 (FIG. 5) upon which to interpret both the absolute and relative positions of the lesion and the biopsy instrument. In general, for cases in which the three-dimensional acoustic impedance volume is processed to compute a composited two-dimensional image therefrom, it is preferable for the composition angle to correspond to the physical angle of the display screen that is displaying that two-dimensional image on the handheld ultrasound scanning device.

Figure 7:
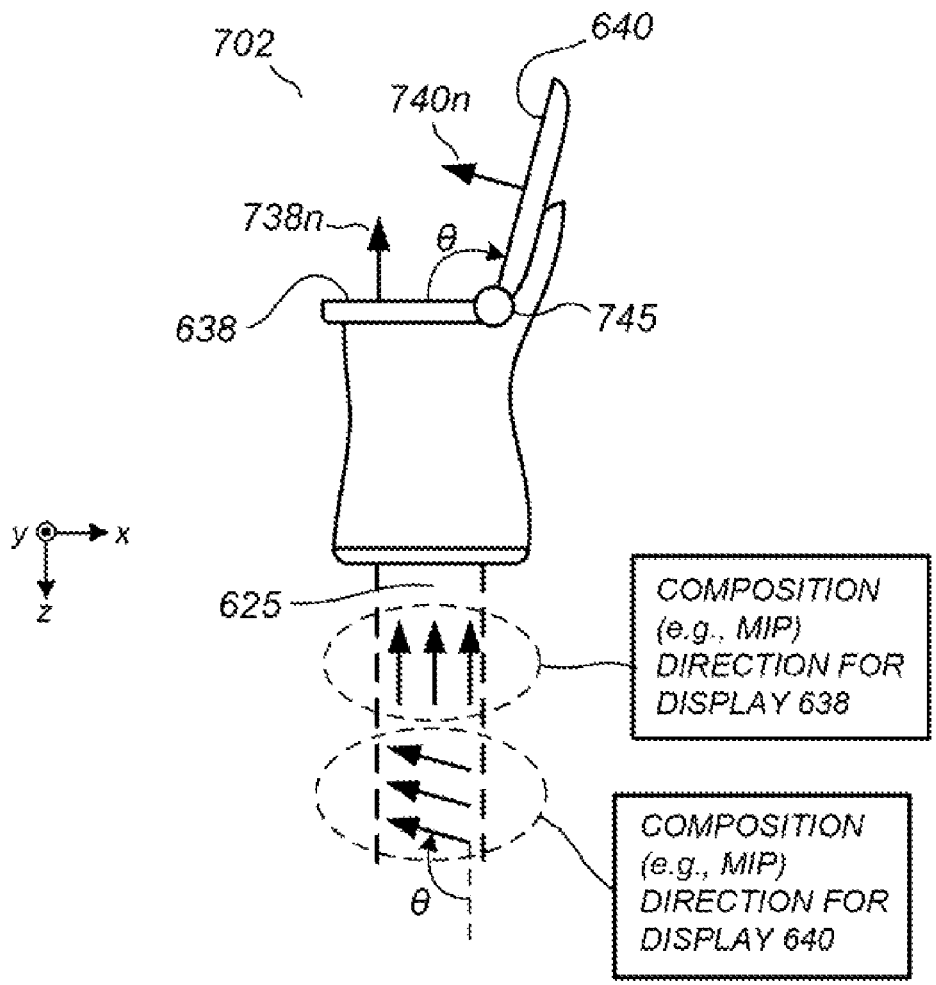
FIG. 7 illustrates a side view of a handheld ultrasound scanning apparatus according to a preferred embodiment.

FIG. 7 illustrates a side view of a handheld ultrasound scanning apparatus 702 according to a preferred embodiment, which is similar to the handheld ultrasound scanning apparatus 602 of FIG. 6, supra, including the first display screen 638 and second display screen 640, but with the addition of an angle detector 745 for detecting an angle θ between the first display screen 638 and second display screen 640. The angle detector 745 can implemented in any of a variety of known ways ranging from a simple potentiometer coupled to a hinged joint between the first display screen 638 and second display screen 640, to a gyro-based, magnetically based, or optically based angle detection scheme. The composition angle for the two-dimensional image on display screen 638 will remain constant at the angle of the normal vector 738n, while the composition angle for the two-dimensional image on display screen 640 will be the angle of the normal vector 740n, which will vary as the opening angle θ varies according to the desired position of the user. Preferably, the compositing angle is varied in real time as the opening angle θ is changed by the user. A unique and spatially intuitive viewing experience is provided, especially when the user tilts the angle θ by modest amounts in a back-and-forth manner, in which case there is a real-time parallax effect (due to the changing composition angles) that is highly helpful in intuitively assessing the relative positions of tissue structures and the biopsy instrument position.

In an alternative preferred embodiment, an actuator (not shown) is provided that automatically changes the angle θ by small amounts so that the spatially intuitive parallax effect can take place without the user themself (or an assistant) needing to manually vary the opening angle θ. In still another alternative preferred embodiment, responsive to an optional user control input (not shown), the physical opening angle θ is kept constant at the user-selected angle, while the compositing angle is automatically varied in software at a relatively slow rate (e.g., 0.5 Hz) between (θ−Δθ) and (θ+Δθ), where Δθ can be about 10 degrees or other user-selectable amount, thereby providing the spatially intuitive parallax effect without requiring manual variation of the opening angle θ.

Figure 8:
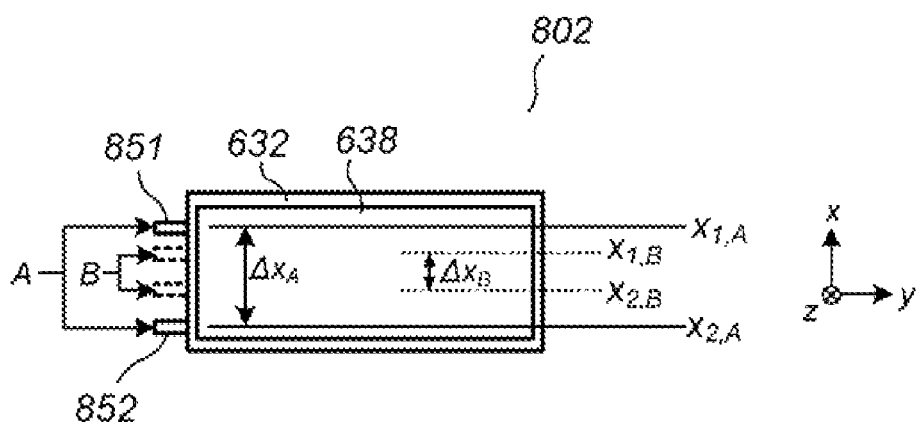
FIG. 8 illustrates a top view of a handheld ultrasound scanning apparatus according to a preferred embodiment.

FIG. 8 illustrates a top view of a handheld ultrasound scanning apparatus 802 according to a preferred embodiment which is similar to the handheld ultrasound scanning apparatus 602 of FIG. 6, supra, but with the addition of user-slidable tabs 851 and 852 positioned alongside the display screen 638. (The lid 634 and backstop feature 608a of FIG. 6 are omitted from the drawing of FIG. 8 for clarity of presentation.) When the user positions the slidable tabs 851-852 in disposition "A", the ultrasound transducer is translated between the corresponding points $x_{1,A}$ and $x_{2,A}$ in the x-direction, which are spaced apart by a first distance $\Delta x_A$. When the user positions the slidable tabs 851-852 more closely together in disposition "B", the ultrasound transducer is translated between the corresponding points $x_{1,B}$ and $x_{2,B}$ that are more closely spaced together. The farther-apart disposition "A" may be used for with a slower probe translation frequency (e.g., between 0.5 Hz-3 Hz) as during a "scout" process where the basic beginning positions of the biopsy instrument and lesion are established, while the closer-together disposition "B" may be used once the user has narrowed down the specific region of interest and is desirous of a faster volume refresh rate (e.g., between 10 Hz-30 Hz) for faster visual feedback during crucial manipulations of the biopsy instrument. In an alternative preferred embodiment (not shown), the display screen 638 can be a touch-sensitive display, and the functionality of the slidable tabs 851-852 realized in a controlling software applet that recognizes, for example, two-fingers touching the screen simultaneously. If the fingers are recognized as sliding apart on the touchscreen, then Δx is increased and the probe translation frequency is decreased, whereas if the fingers are recognized as sliding together on the touchscreen, then Δx is decreased and the probe translation frequency is increased.

Whereas many alterations and modifications of the present invention will no doubt become apparent to a person of ordinary skill in the art after having read the foregoing description, it is to be understood that the particular embodiments shown and described by way of illustration are in no way intended to be considered limiting. By way of example, although the ultrasound transducer that is mechanically translated within the housing for at least one preferred embodiments supra is a linear array ultrasound transducer, in other preferred embodiments it can be a different ultrasound transducer type such as a 1.25D, a 1.5D, or a 2D ultrasound transducer. By way of further example, although described primarily in terms of percutaneous biopsy of the breast, one or more of the above-described preferred embodiments are readily applicable and/or adaptable for compressive biopsy for the arm, the leg, the neck, the abdomen, or other human or animal body part.

By way of still further example, although described supra primarily in terms of purely freehand biopsy in which the biopsy instrument is entirely separate from the handheld ultrasound scanning apparatus, in other preferred embodiments there is also provided a biopsy guide that mechanically links the biopsy instrument to the handheld ultrasound transducer for increased stability, such as those described in the commonly assigned US06695786B2, which is incorporated by reference herein.

By way of further example, although advantageous in the context of freehand ultrasound assisted biopsy procedures, one or more of the above-described preferred embodiments is also advantageous for facilitating certain types and portions of the breast brachytherapy process. Breast brachytherapy involves the insertion of a small radioactive seed into the breast, usually at the site of a tumor that has recently been removed, for temporary radiation treatment of the surrounding tissue. The temporary radiation treatment is often performed in multiple sessions over the course of several days, the radioactive seed(s) being inserted at the beginning of each session and removed at the end of each session. Typically, a catheter-based structural framework is formed prior to the first session to ease the process of delivering the radioactive seed(s) to and from the target site over the coming sessions, and for ensuring proper separation between the delivered seed and the surrounding tissue. In one common type of breast brachytherapy process often called catheter-balloon brachytherapy, the catheter-based structural framework is formed by freehand insertion of a hollow needle or other hollow applicator device ("brachytherapy applicator device") into the breast until its tip is near a desired site of the seed, after which a small inflatable balloon or balloon-like element and a small attached catheter ("catheter-balloon assembly") are delivered through the lumen of the brachytherapy applicator device to the desired site. After appropriate "inflation" with saline, the balloon or balloon-like element will serve as the seed holder during the sessions and the attached catheter will be used to deliver the radioactive seed(s) thereto and therefrom. As with percutaneous breast biopsy procedures, there is a need to provide high-quality volumetric ultrasound image guidance for the percutaneous freehand manipulation of a generally elongate brachytherapy applicator device toward the desired radiation site, at the same time, in view of the generally undulous nature of the breast surface, there is also a need for local stabilization of the breast subvolume that is being image. It has been found that the uniquely desirable combination of slidability and grippability along the scanning surface provided by a handheld volumetric ultrasound scanning device according to one or more of the preferred embodiments supra is also particularly advantageous for use in ultrasound guidance of a brachytherapy applicator device toward the desired radiation site.

By way of even further example, although particularly advantageous in the context of freehand ultrasound assisted biopsy procedures, one or more of the above-described preferred embodiments can be advantageous employed in any of a variety of non-biopsy related ultrasound imaging contexts such as, but not limited to, real-time volumetric cardiac imaging and real-time volumetric fetal imaging. Therefore, reference to the details of the embodiments are not intended to limit their scope, which is limited only by the scope of the claims set forth below.

What is claimed is:

1. An apparatus for ultrasonically scanning a tissue volume, comprising:
   a processor; and
   a handheld ultrasound device, comprising:
      a casing configured and dimensioned for single-handed manipulation within which is disposed a mechanically oscillated ultrasound transducer, said casing having a top surface and a bottom opening;
      a texturably couplant-porous material sheet extending across said bottom opening for compressively contacting a surface of the tissue volume, said ultrasound transducer being mechanically translated across the material sheet while in contact therewith, said ultrasound transducer acquiring ultrasonic scans of the tissue volume downward through said material sheet during said mechanical translation, said processor processing the ultrasonic scans to generate an ultrasound volume representative of an ultrasonic property of the tissue volume;
      a first ultrasound display integral with an upper surface of said casing for displaying a first two-dimensional image derived from the ultrasound volume;
      a lid hingably coupled to said casing near said first ultrasound display, said lid being manually closable to cover the first display and manually openable to uncover the first display and remain at a user-adjustable opening angle relative thereto;
      a second ultrasound display integral with an inner surface of said lid for displaying a second two-dimensional image derived from the ultrasound volume when said lid is in an open position; and
      an angle detection device for detecting said opening angle of said lid;
   wherein said processor computes said first two-dimensional image by compositing said ultrasound volume in a generally upward direction, and wherein said processor computes said second two-dimensional image by receiving said detected opening angle and compositing said ultrasound volume in a first direction faced by said second ultrasound display as determined by said detected opening angle.

2. The apparatus of claim 1, wherein said first two-dimensional image comprises a three-dimensional rendering of said ultrasound volume as composited in said generally upward direction, and wherein said second two-dimensional image comprises a three-dimensional rendering of said ultrasound volume as composited in said first direction.

3. The apparatus of claim 2, wherein said three-dimensional renderings are maximum intensity projection images.

4. The apparatus of claim 1, wherein said texturably couplant-porous material sheet comprises at least one of a taut fabric sheet and a vented membrane.

5. The apparatus of claim 1, wherein said texturably couplant-porous material sheet comprises a taut fabric sheet.

6. The apparatus of claim 5, wherein said taut fabric sheet is substantially inelastic and comprises a material selected from the group consisting of: polyester organza materials, polyester chiffon fabrics, and cloth fabrics.

* * * * *